(12) United States Patent
Nelson et al.

(10) Patent No.: US 8,808,233 B2
(45) Date of Patent: Aug. 19, 2014

(54) MULTIPLE FLUID COMBINING SYRINGE

(76) Inventors: Laurie Ausley Nelson, Largo, FL (US); Shirley Marie Spelich, Seminole, FL (US)

(*) Notice: Subject to any disclaimer, the term of this patent is extended or adjusted under 35 U.S.C. 154(b) by 232 days.

(21) Appl. No.: 13/445,266

(22) Filed: Apr. 12, 2012

(65) Prior Publication Data

US 2013/0274716 A1  Oct. 17, 2013

(51) Int. Cl.
*A61M 37/00* (2006.01)
*A61M 5/315* (2006.01)
*A61M 5/00* (2006.01)
*A61M 31/00* (2006.01)

(52) U.S. Cl.
USPC ............. 604/88; 604/231; 604/234; 604/518

(58) Field of Classification Search
CPC ............. A61M 5/19; A61M 5/31596; A61M 5/31511; A61M 5/284; A61M 5/2448; A61M 2005/31598; A61M 2005/1787; A61M 2005/3201
USPC ............. 604/825, 416, 518, 82–92, 231–233; 433/89–90
See application file for complete search history.

(56) References Cited

U.S. PATENT DOCUMENTS

| | | | | |
|---|---|---|---|---|
| 3,749,084 A | * | 7/1973 | Cucchiara | 600/575 |
| 4,609,371 A | * | 9/1986 | Pizzino | 604/191 |
| 4,915,695 A | * | 4/1990 | Koobs | 604/191 |
| 5,053,019 A | * | 10/1991 | Duffy | 604/232 |
| 5,697,903 A | * | 12/1997 | Fischer | 604/82 |
| 2007/0020754 A1 | * | 1/2007 | Yuge et al. | 435/325 |

* cited by examiner

*Primary Examiner* — Rebecca E Eisenberg
(74) *Attorney, Agent, or Firm* — Inventions International Inc.; Tiffany C. Miller (57) ABSTRACT

A combining syringe wherein multiple fluids are dispensed through a primary plunger into a primary cylinder when a force is applied to the secondary plunger shaft. The fluids are combined and dispensed from the primary cylinder's attaching end when a force is applied to the primary plunger shaft. The primary plunger shaft has a primary plunger attaching end opposite a primary pressure applying end. The primary plunger is connected to the primary plunger attaching end. The primary plunger shaft accepts a secondary cylinder and secures it with an attaching element. The secondary cylinder has a secondary plunger receiving end opposite a dispensing end. The secondary cylinder's dispensing end is inserted into an opening of the primary plunger. The secondary plunger shaft has a secondary plunger attaching end opposite a secondary pressure applying end. The secondary plunger is connected to the secondary plunger attaching end.

19 Claims, 8 Drawing Sheets

MULTIPLE FLUID COMBINING SYRINGE

BACKGROUND OF THE INVENTION

1. Field of the Invention

This invention relates to a combining syringe in which an administrator applies a pressure great enough to force a fluid from a secondary cylinder into a primary cylinder where the fluid is combined and then dispensed through an attaching end. The present invention relates particularly to a combining syringe configured to receive a plurality of cylinders through a slidable plunger of a primary cylinder.

2. Background Art

A multiple fluid combining syringe is used in the preparation of multiple sterile products which are combined into a cylinder prior to being dispensed into the injection site. Formerly, syringes dispensing multiple fluids are seen to incorporate excess parts including a valve assembly having a valved stopper and a valve actuator as described in U.S. Pat. No. 6,997,910.

Thus, there is a need for a multiple fluid combining syringe with an improved configuration, eliminating the need for additional parts, valve assemblies, and eliminating the associated costs for manufacturing and assembling these parts.

Prior art syringe devices are seen to incorporate a sliding piston having a valve as described in U.S. Pat. No. 7,635,344. Before the fluids are combined, a user slides the piston from a first position to a second position in the chamber. When the valve is opened by a user, the fluid is guided into a chamber. This requires a user to perform the additional step of opening the valve which is time consuming. In addition, the valve may fail, rendering the syringe inoperable.

Therefore, there is a need for an improved combining syringe that eliminates the need of having a valve system which reduces the possibility of the system failing.

Maaskamp et al. teach in U.S. Patent Application No. 20080275403 a dual syringe assembly comprising a housing having a pair of proximal ports and a distal port, a primary one way valve within the primary proximal chamber, and a secondary one way valve within the secondary proximal chamber. A user sequentially dispenses a fluid comprising the steps of attaching a connector valve assembly to a primary syringe and a secondary syringe, the connector valve assembly having a primary and secondary one way valve, and a user initially depressing the primary syringe to release the fluid through the primary one way valve and then depressing the secondary syringe. This configuration does not allow a user to combine the fluids.

Hence, there is a need for a syringe having a configuration to accommodate a plurality of separated fluids to be dispensed through a single plunger. The improved method will eliminate the need for additional parts such as a valve stopper and a valve actuator and will allow for combining of fluids prior to dispensing.

BRIEF SUMMARY OF THE INVENTION

The long-standing but heretofore unfulfilled need for a combining syringe configured to receive a secondary cylinder through a slidable primary plunger within a primary cylinder, is now met by a new, useful, and non-obvious invention.

The combining syringe includes a primary cylinder having a primary plunger configured to receive a secondary cylinder having a secondary plunger. Additional fluids may be added to the primary cylinder when an administrator inserts a secondary cylinder's dispensing end into the opening of the primary plunger. When a force is applied to the secondary plunger shaft, the fluid is dispensed through the primary plunger and combined in the primary cylinder. The administrator then applies a force to the primary plunger shaft to dispense fluid out from the primary cylinder's attaching end.

In a first embodiment, the novel combining syringe includes a primary cylinder having an attaching end opposite of a primary plunger receiving end. A primary plunger is slidable within the primary plunger receiving end of the primary cylinder. The primary plunger is connected to the primary plunger attaching end of the primary plunger shaft. The primary plunger is configured to create a pressure great enough to dispense a fluid out of the primary cylinder's attaching end when a force is applied to an end of the primary plunger shaft. The primary plunger shaft has a longitudinal body having a primary plunger attaching end opposite of a primary pressure applying end. The primary plunger shaft has an attaching element to secure a secondary cylinder. The secondary cylinder is configured to dispense a fluid through an opening of the primary plunger. The secondary cylinder has a secondary plunger receiving end that is located opposite of the dispensing end. The secondary plunger receiving end receives the secondary plunger shaft. The secondary plunger shaft has a secondary plunger attaching end opposite of a secondary pressure applying end. The secondary plunger is connected to the secondary plunger attaching end. The secondary plunger shaft is configured to create a pressure great enough to force a fluid into the primary cylinder when a force is applied to the secondary pressure applying end.

Although the preferred embodiment for the combining syringe includes a secondary cylinder being inserted into the primary plunger, the scope of this invention should not be limited to a secondary cylinder, but should also encompass a third cylinder, a fourth cylinder, and a fifth cylinder adapted to dispense multiple fluids through a primary plunger into the primary cylinder.

In a second embodiment, the novel combining syringe of the first embodiment has a second, third, fourth, and fifth cylinder adapted to fit within the primary plunger and is configured to force a fluid through the primary plunger when a force is applied to the second, third, fourth, and fifth plunger shaft. An administrator inserts the second, third, fourth, and fifth cylinder's dispensing end into a first, second, third, and fourth opening of the primary plunger. When a force is applied to the second, third, fourth, and fifth plunger shafts, the multiple fluids are dispensed through the primary plunger and are combined in the primary cylinder.

In a third embodiment, the combining syringe has a primary cylinder including, but is not limited to, the sizes of 20 ml., 30 ml., and 60 ml. having at least one section of the primary plunger shaft accommodating a secondary cylinder. The secondary cylinder includes, but is not limited to, a sterile, latex free syringe of 0.5 ml. in size. The primary cylinder is larger than the secondary cylinder, wherein the secondary cylinder is inserted into the primary plunger.

In a fourth embodiment, the combining syringe includes a primary plunger shaft divided into four longitudinal sections where each section receives a syringe. Four syringes are inserted into the primary plunger shaft and are positioned so that the dispensing end dispenses fluid through the primary plunger into the primary cylinder.

In a fifth embodiment, the primary plunger shaft of the fourth embodiment has an attaching element including, but not limited to, a band or a clamp. The attaching element secures one or more syringes into the primary plunger shaft. When an administrator applies a force to the primary pressure applying end of the primary plunger shaft, it will cause the primary plunger to slide within the primary cylinder. The attaching element will prevent the one or more syringes from moving freely within the primary plunger shaft and secure the one or more syringes into the primary plunger.

In a sixth embodiment the combining syringe includes a primary plunger shaft having a primary pressure applying end opposite of an attaching end. A primary plunger is connected to the primary plunger attaching end including but not limited to, a rubber, non-latex material, having four openings to receive the dispensing end of the four syringes. The opening of the primary plunger includes, but is not limited to, a hole or a slit. A variety of differing sized secondary cylinders are accepted by the opening due to the plurality of reliefs radiating from its circumference. This allows for the material of the first plunger to conform to the circumference of the secondary cylinder. A secondary cylinder's dispensing end is inserted into the opening of the primary plunger. When an administrator applies a force to the secondary pressure applying end of the secondary plunger shaft, fluid is dispensed through the primary plunger into the primary cylinder.

In a seventh embodiment, the combining syringe includes a primary cylinder having a leur-lock connection fitting located on the attaching end. The leur-lock connection fitting will accommodate, but is not limited to, a needle or tubing.

In an eighth embodiment, the combining syringe includes a secondary plunger shaft having a longitudinal body whereby a secondary plunger attaching end is opposite of a secondary pressure applying end with at least a portion that is of a different color than a third plunger shaft.

These eight (8) embodiments are illustrative of the invention and are not exclusive thereof. As combining syringe manufacturers add additional or different features to the primary plunger shaft, still further attaching elements may be required in future embodiments of the invention, but all such future embodiments are within the scope of this invention.

Moreover, as mentioned earlier, each of the eight (8) illustrative embodiments of the combining syringe are adapted for multiple fluids to be combined in the primary cylinder by the force of an administrator upon the secondary plunger shaft, where the fluids are dispensed from the attaching end of the primary cylinder when a force is applied to the primary plunger shaft. The mixing syringe includes a plurality of syringes therein.

For example, a large syringe, including but not limited to, a latex free plastic material, is wrapped as a sterile product having four small sterile, latex free syringes also separately wrapped. The four small syringes contain fluids to be mixed within the larger syringe. The large syringe may be filled with a fluid or may be kept empty for the mixing of the smaller syringes. The large syringe has a primary plunger which receives, but is not limited to, four smaller syringes of fluid.

The primary plunger shaft is divided into longitudinal sections accommodating a second, third, fourth, and a fifth cylinder in a separated position. For example, the dispensing end of the secondary cylinder is inserted an opening of the primary plunger. This opening includes, but is not limited to, a hole or a slit which conforms to the shape of the syringe to create a liquid-tight seal, preventing fluids of the primary syringe from leaking out. The primary plunger includes, but is not limited to, a rubber, non-latex material.

More particularly, it is through the primary plunger opening where the fluid from the smaller syringe is dispensed through to the large syringe. Before or during the act of an administrator dispensing a fluid from the large syringe from the attaching end, requires a force to be applied to the secondary pressure applying end of the smaller syringe plunger shaft to dispense a sterile addition of up to four additional fluids into the large syringe.

In another example, the combining syringe's primary cylinder has a leur-lock connection fitting located on the attaching end. A needle or tubing is attached to the attaching end. In a first example, the fluid is dispensed through the needle into an injection site. This injection site includes, but is not limited to a recipient. In a second example, the fluid is dispensed through tubing which empties into a sterile bag.

Thus, a force is applied to the primary plunger shaft and the plurality of syringes are positioned to dispense a fluid through a primary plunger by a force applied to the second, third, fourth, and fifth plunger shafts by an administrator. The force of an administrator on the primary plunger as well as the second, third, fourth, and fifth plunger, will work with all currently known single dose disposable syringes and in view of this disclosure any future changes to the combining syringe components can be met.

In addition to the aforesaid embodiments of the combining syringe, the combining syringe includes multiple additional improvements as well.

A first improvement is a primary plunger modified to accommodate four small syringes to dispense up to four additional fluids through the primary plunger into the primary cylinder. This configuration allows an administrator to quickly dispense multiple fluids through the attaching end of the primary cylinder. The improved configuration makes this device safe for the combining of multiple, sterile, and compatible fluids in a primary cylinder. Convenience is achieved with dispensing the combination of fluids in a single injection to a recipient.

A second improvement is an attaching element connected to the primary plunger shaft. The primary plunger shaft receives a secondary cylinder. The administrator inserts a secondary cylinder into a longitudinal section of the primary plunger shaft and each section of the first plunger shaft contains a clamp securing the secondary cylinder in place. This attaching element is necessary to prevent the secondary cylinder from sliding within the primary cylinder and potentially allowing the primary cylinder fluid to leak through the exposed opening within the primary plunger. Thus, it is understood that the combining syringe receives a second fluid through the primary plunger, where the primary plunger shaft has an attaching element including, but not limited to, a band or a clamp. However, any means of securing a syringe to a primary plunger shaft are within the scope of this invention.

A third improvement is a combining syringe whereby a user applies a force to a secondary plunger shaft having at least a portion that is of a different color than a third, fourth, or fifth plunger shaft. The plunger shafts of the four small syringes have a specific color including, but not limited to, red, green, orange, and blue. An administrator visually verifies the color of a secondary plunger shaft as being filled with a specific fluid. This contributes to a decrease in drug errors by allowing an administrator to confirm for example that fluid "A" in the syringe with the "blue" second plunger shaft and fluid "B" in the syringe with the "red" third plunger shaft.

A first embodiment of the color specific secondary plunger shaft is that it aids in identifying the specific sequence of fluid being dispensed into the primary cylinder where an administrator visually compares the color of the second plunger shaft with the color of a third plunger shaft. For example, the fluid associated with the "blue" second plunger shaft will be initially dispensed into the primary cylinder. Then, the fluid associated with the "red" third plunger shaft will be additionally dispensed into the primary cylinder.

A second embodiment of the color specific second plunger shaft is that it contains a user specific bar code. For example, when a syringe is sent from location "A" to location "B", the bar code attached to the syringe will ensure it is received at the proper location. This bar code will decrease possible erroneous administration to another recipient, thus, improving the safety of a recipient.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustrating specific embodiments by which the invention may be practiced. It is to be understood that other embodiments may be utilized and structural changes may be made without departing from the scope of the invention.

Terms

As used herein, the term "cylinder", refers to any syringe barrel capable of containing a fluid. Examples include, but are not limited to, latex free plastic.

As used herein, the term "opening", refers to any orifice on the primary plunger, capable of accepting a secondary cylinder. Examples include, but are not limited to, a hole or a slit.

As used herein, the term "attaching element", refers to any self-latching method an administrator could perform to secure a secondary cylinder within a primary plunger shaft. Examples include, but are not limited to, a clamp or a band.

As used herein, the term "fluid", refers to any substance that has the ability to flow through a primary plunger into a primary cylinder, to be dispensed out of attaching end. Examples include, but are not limited to, a fluid, a medication, a syringe additive, or a sterile substance.

As used herein, the term "force", refers to any pulling or pushing motion that can slidably move a plunger within a cylinder to dispense a fluid, is within the scope of this invention. Examples include, but are not limited to, a vertical or horizontal force or a diagonal force applied by an administrator.

As used herein, the term "color specific", refers to any color that corresponds to a second, third, fourth, or fifth plunger shaft. At least a portion of the plunger shaft is color specific to correspond to a fluid in a second, third, fourth, or fifth cylinder. Color examples include, but are not limited to, red, green, orange, or blue.

As used herein, the term "reliefs", refers to any cut or separation of the primary plunger surrounding the opening, allowing the circumference of the opening to expand and fit different sized secondary cylinders.

Figure 1A:
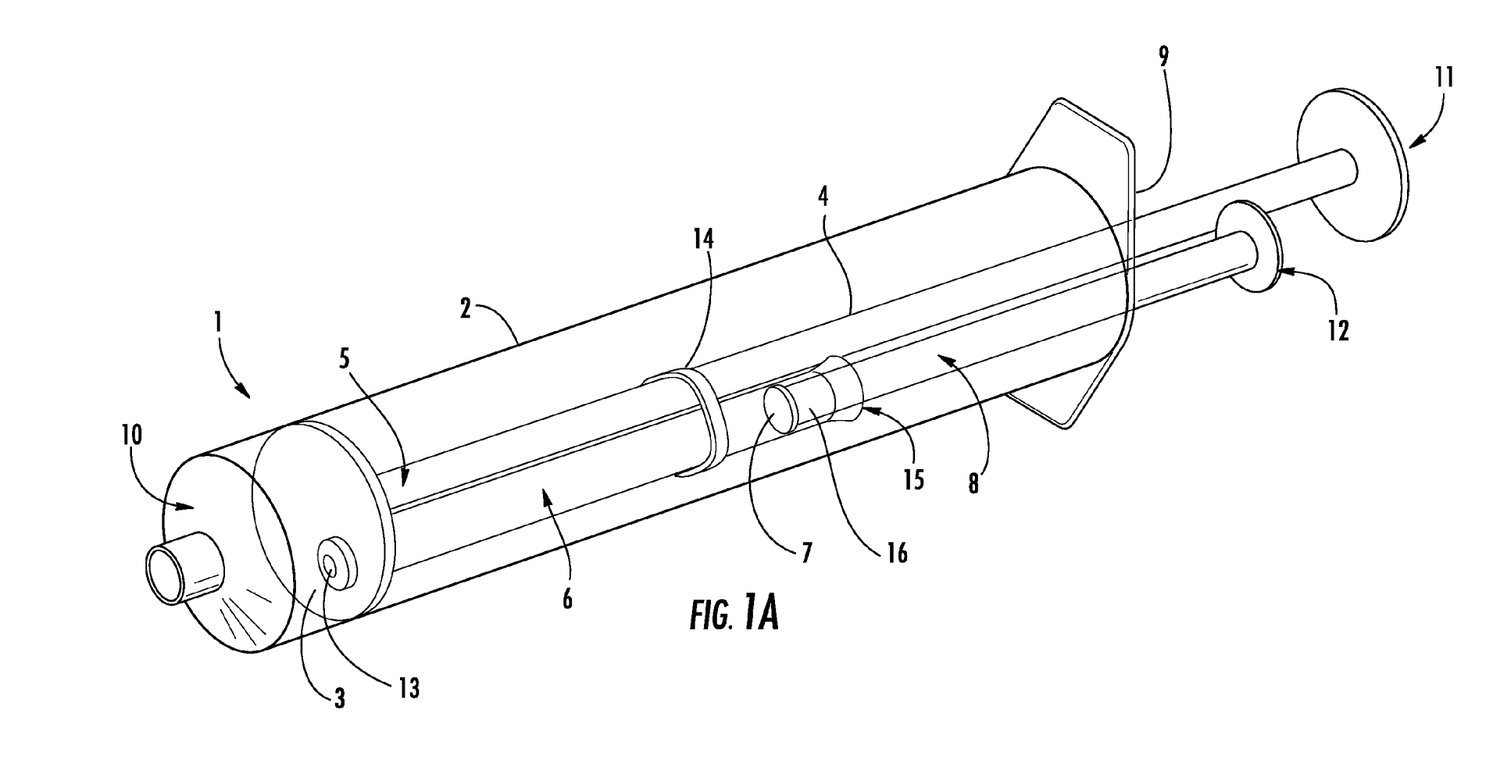
FIG. 1A is a side perspective view of the novel combining syringe.
Figure 1B:
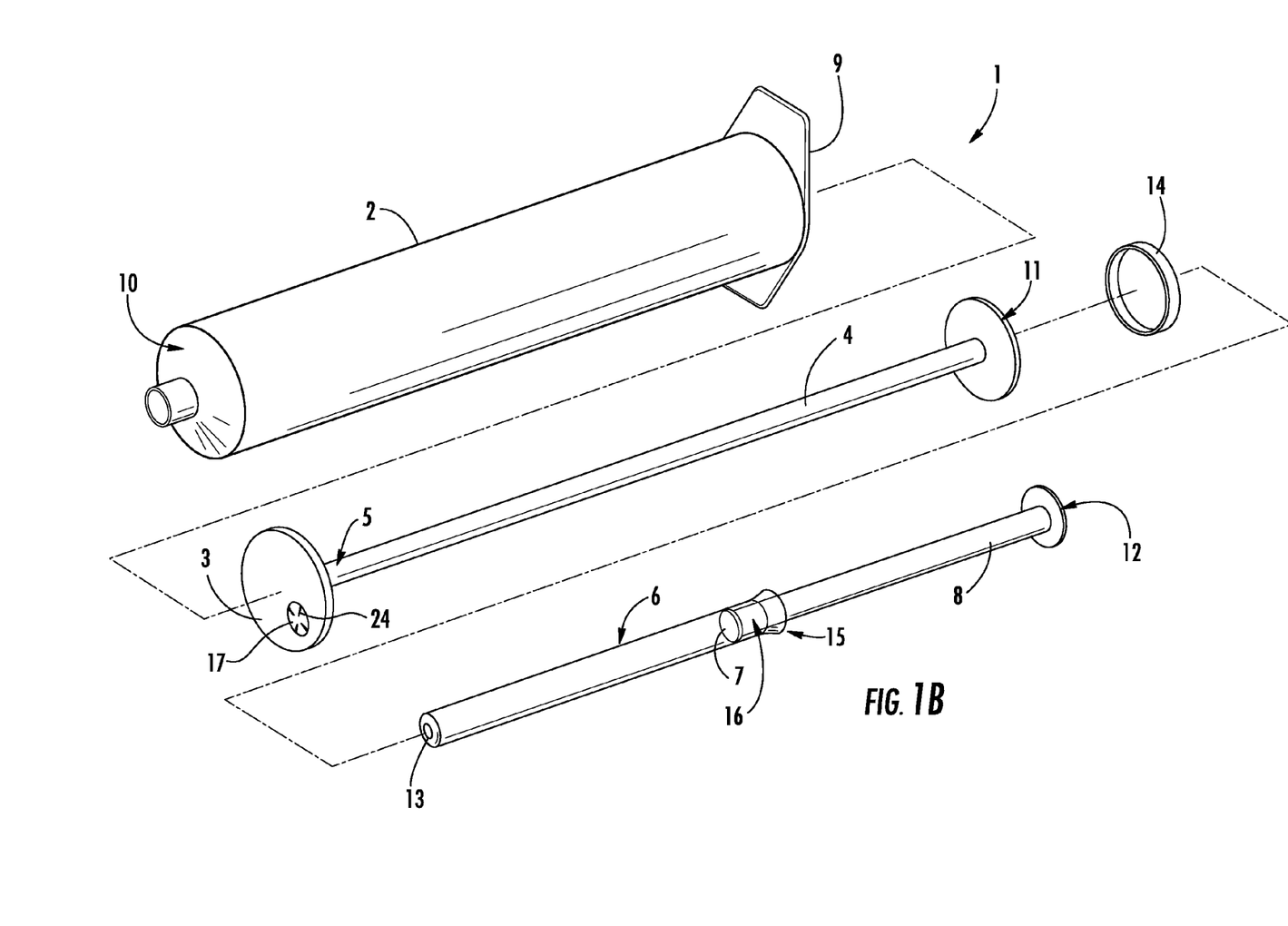
FIG. 1B is an inside exploded perspective view of the combining syringe components.

Referring now to FIGS. 1A and 1B, it will there be seen that the reference numeral 1 denotes an illustrative embodiment of the novel combining syringe adapted to dispense a fluid through a primary plunger into a primary cylinder. Novel combining syringe 1 is made by primary cylinder 2 having a primary plunger 3 slidable within primary plunger receiving end 9. Combining syringe 1 is not limited to the preferred embodiment as shown and may encompass any size or configuration to dispense a fluid from attaching end 10. Primary plunger shaft 4 has a primary pressure applying end 11 and a primary plunger attaching end 5. The primary plunger 3 is located on the primary plunger attaching end 5. Primary plunger shaft 4 has attaching element 14 configured to secure a secondary cylinder 6. Secondary cylinder 6 has a dispensing end 13 opposite of a secondary plunger receiving end 15. Secondary plunger shaft 8 has a secondary pressure applying end 12 opposite a secondary plunger attaching end 16. The secondary plunger 7 is located on the secondary plunger attaching end 16.

In FIG. 1B, dispensing end 13 of secondary cylinder 6 allows passage of fluid to flow through the opening 17 of primary plunger 3 into primary cylinder 2. The plurality of reliefs 24 accommodates various sized secondary cylinders 6.

Figure 2A:
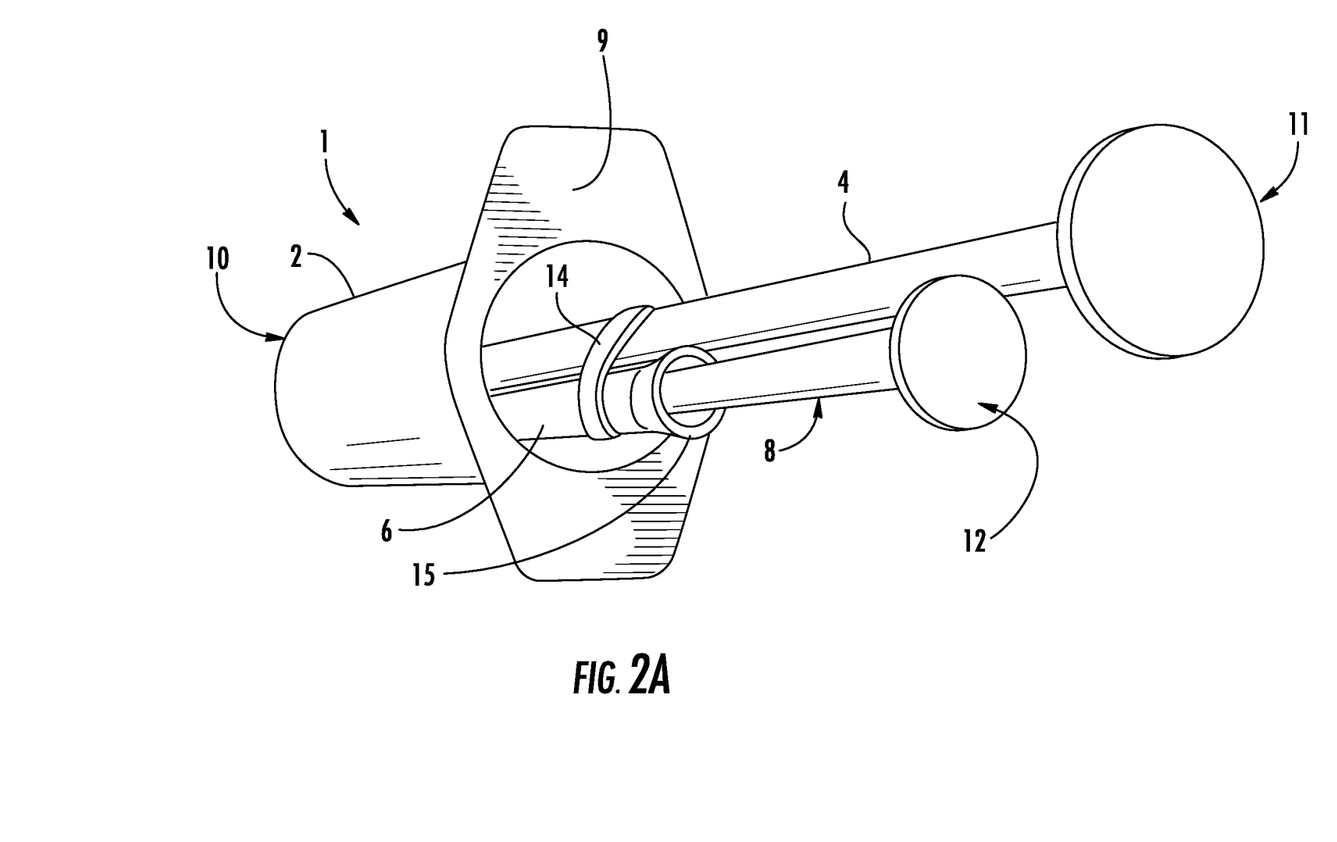
FIG. 2A is a rear perspective view of a first embodiment of the novel combining syringe.
Figure 2B:
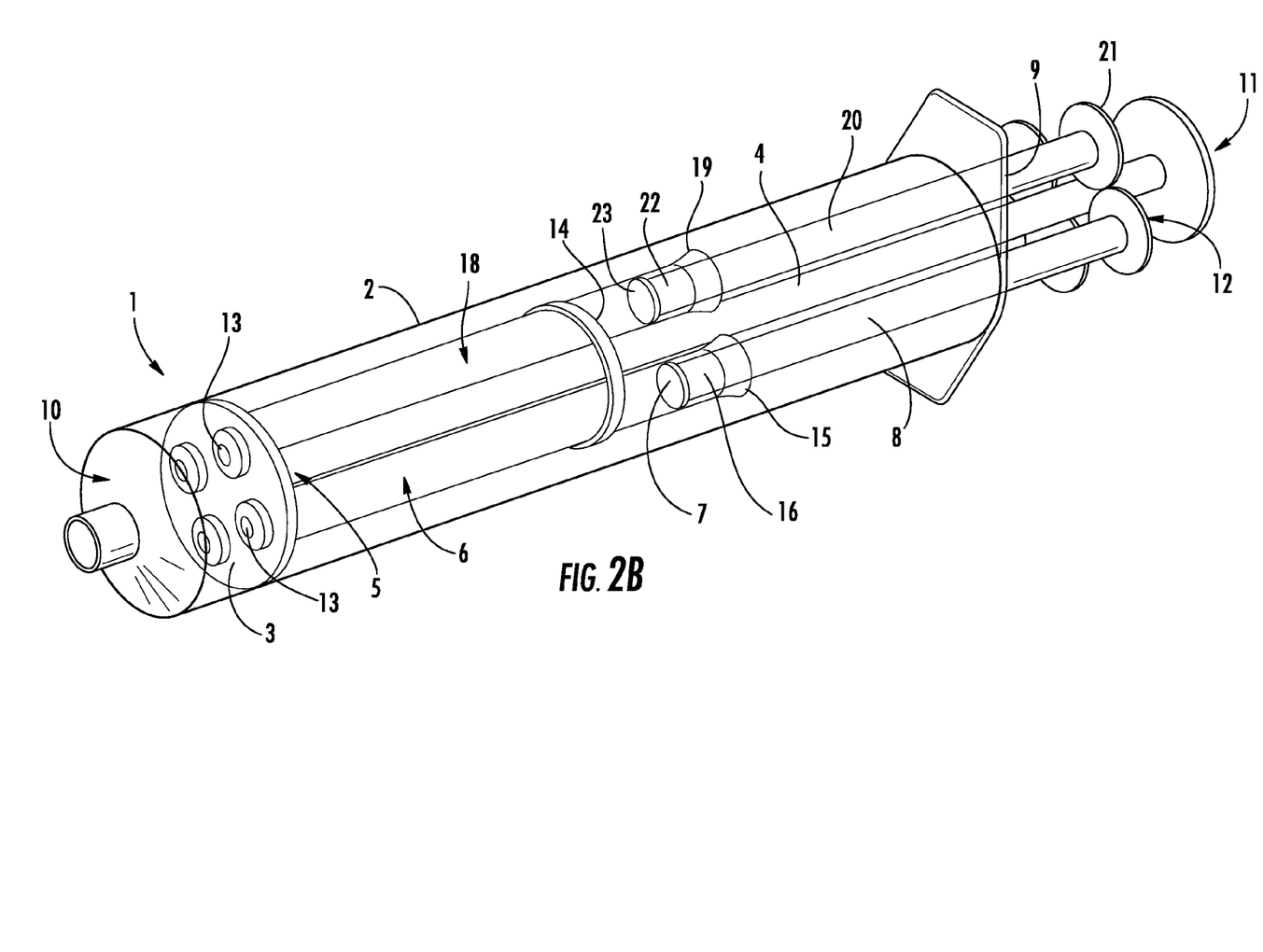
FIG. 2B is a side perspective view of a second embodiment of the novel combining syringe.
Figure 2C:
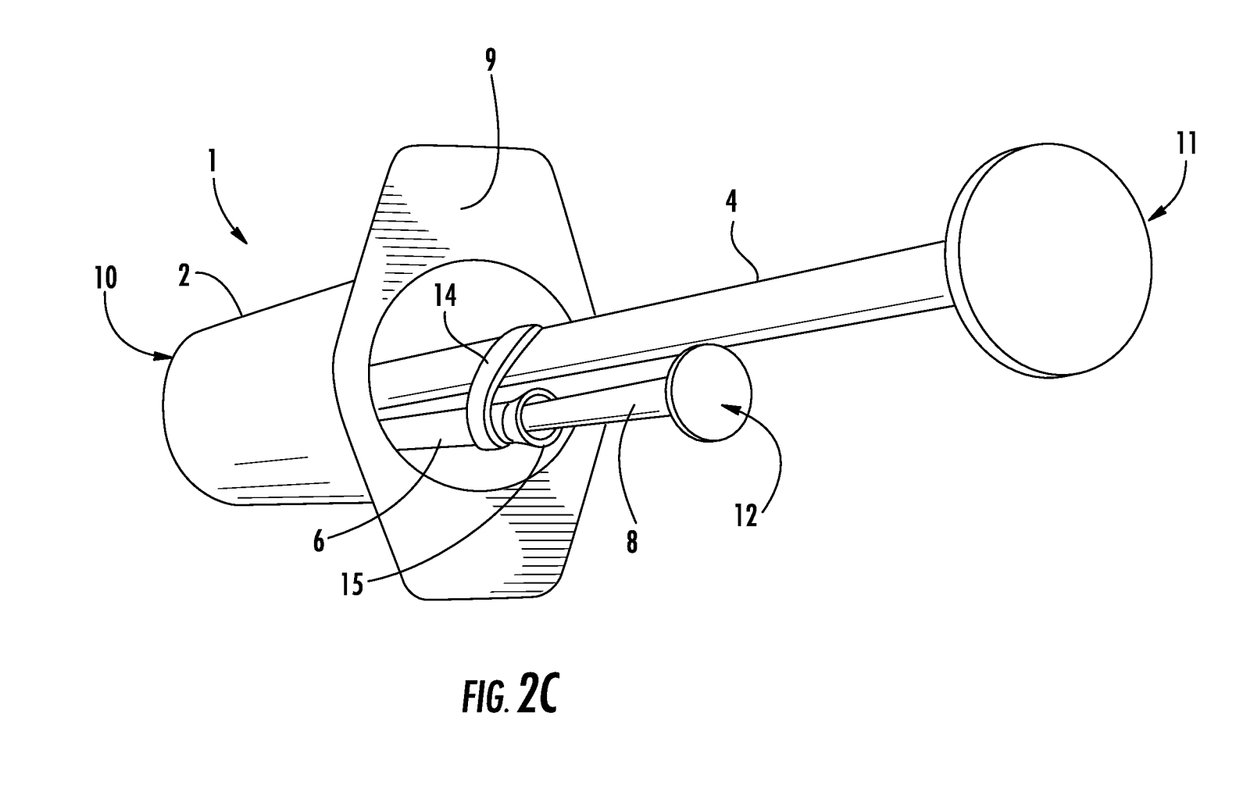
FIG. 2C is a rear perspective view of a third embodiment of the novel combining syringe.
Figure 2D:
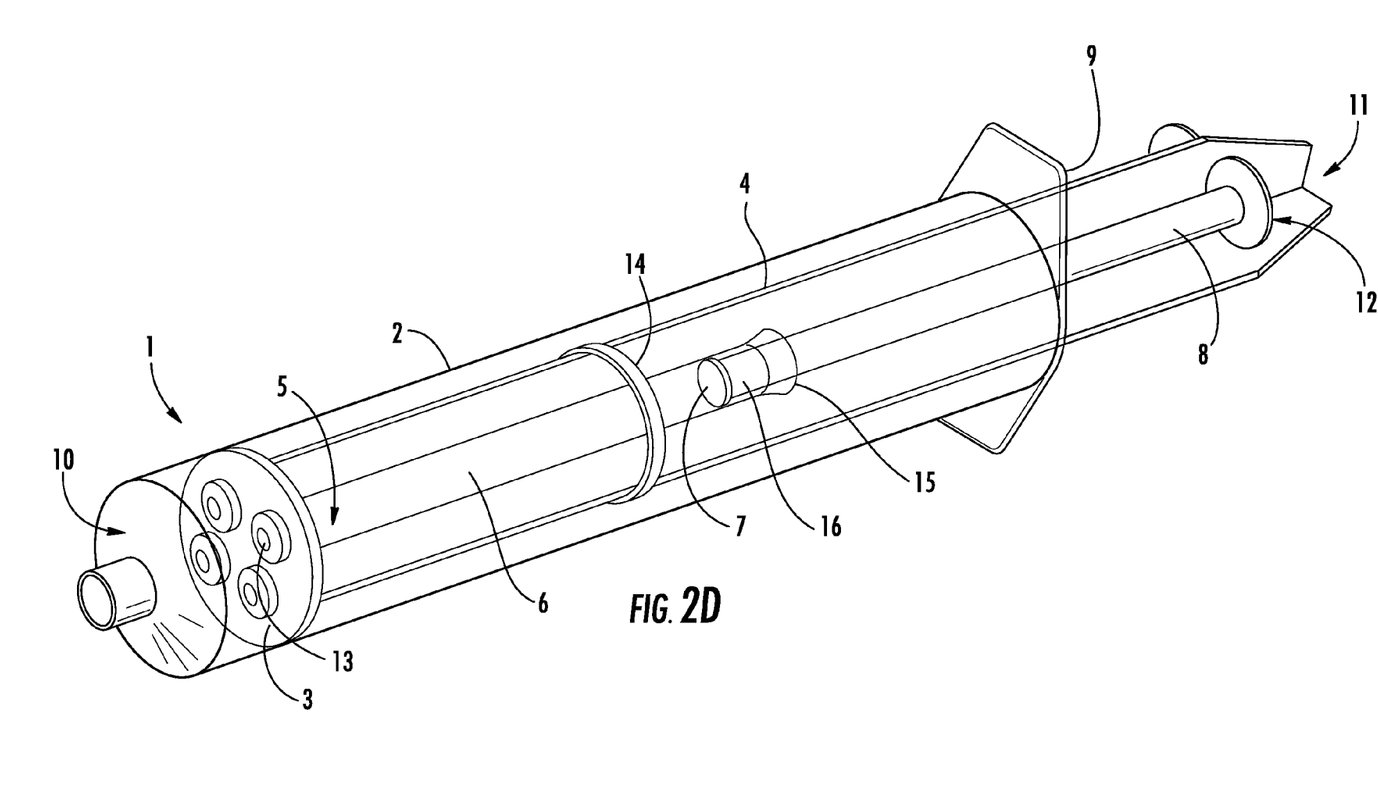
FIG. 2D is a side perspective view of a fourth embodiment of the novel combining syringe.
Figure 2E:
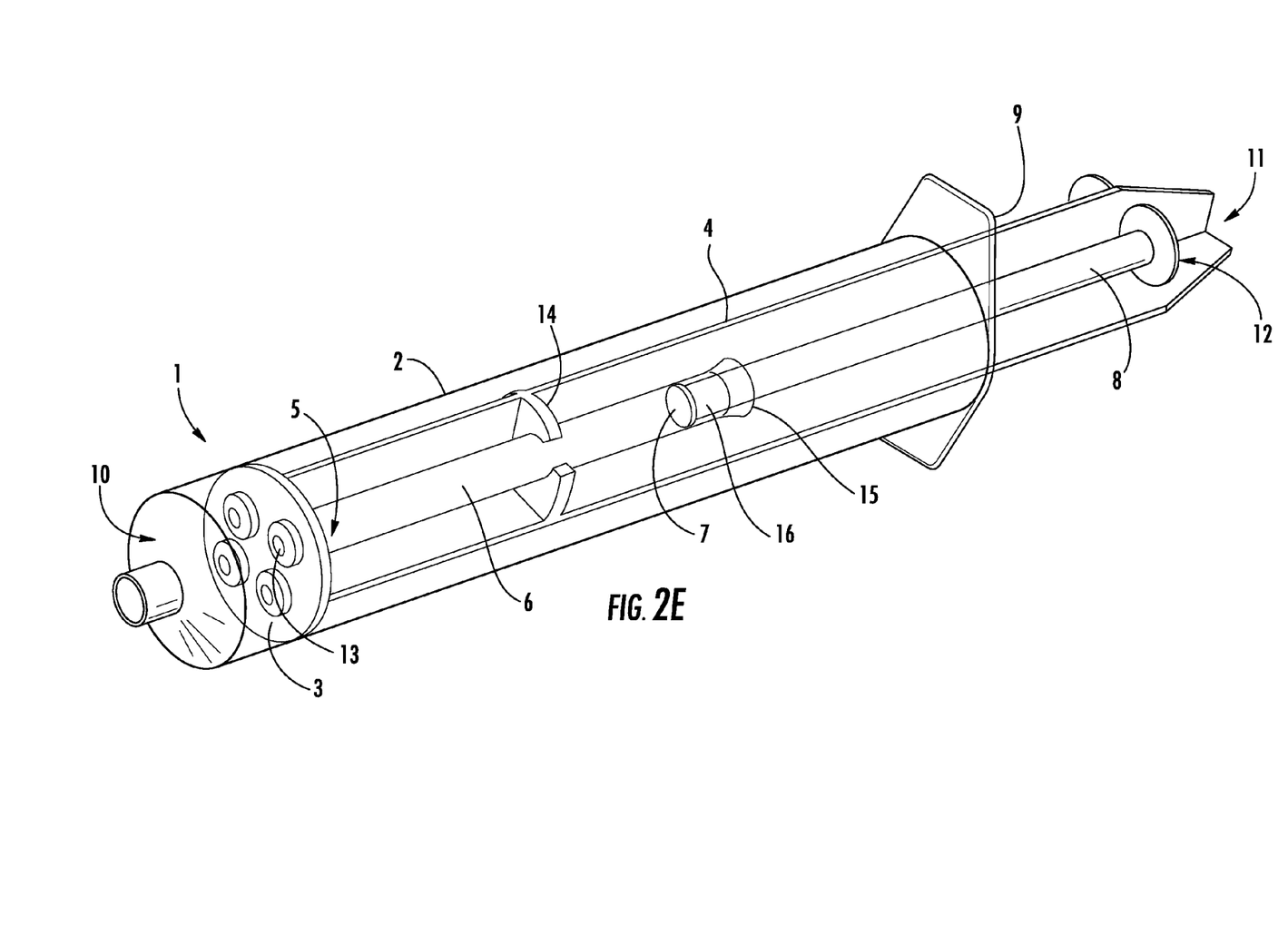
FIG. 2E is a side perspective view of a fifth embodiment of the novel combining syringe.

Still further novel features are perhaps best depicted in FIGS. 2A and 2C. Combining syringe 1 has a primary plunger shaft 4. Primary plunger shaft 4 has a primary pressure applying end 11 and is slidable within primary plunger receiving end 9. Primary plunger shaft 4 has attaching element 14 configured to secure a secondary cylinder 6. Secondary cylinder 6 has a secondary plunger receiving end 15. Secondary plunger shaft 8 has a secondary pressure applying end 12 and is slidable within secondary plunger receiving end 15. When a force is applied to secondary pressure applying end 12, the fluid is dispensed into primary cylinder 2. When a force is applied to primary pressure applying end 11, the fluid is dispensed out of attaching end 10.

FIG. 2C depicts combining syringe 1 having primary cylinder 2 with a diameter sufficient to accommodate a secondary cylinder 6. The larger diameter of primary cylinder 2 allows for larger doses of fluid to be dispensed by secondary cylinder 6, substantially eliminating the possibility of infection problem caused by introducing additional syringes.

As perhaps best understood in connection with FIG. 2B combining syringe 1 accommodates up to four additional cylinders of fluid. A secondary cylinder 6 and tertiary cylinder 18 are adapted to fit within the primary plunger 3. When a force is applied to the secondary pressure applying end 12 of secondary plunger shaft 8 and the tertiary pressure applying end 21 of tertiary plunger shaft 20, the fluids are dispensed through the primary plunger 3 into primary cylinder 2 where they are combined. Tertiary plunger shaft 20 has a tertiary pressure applying end 21 opposite of tertiary plunger attaching end 22. Tertiary plunger 23 is connected to tertiary plunger attaching end 22. Tertiary plunger shaft 20 is slidable within tertiary plunger receiving end 19. Attaching element 14 secures secondary cylinder 6 and tertiary cylinder 18 onto primary plunger shaft 4.

Still further novel features are perhaps best depicted in FIGS. 2 D-E. Primary plunger shaft 4 is divided into four longitudinal sections where each section receives a syringe. Attaching element 14 is shown as a supportive band which secures secondary cylinder 6 to primary plunger shaft 4 in FIG. 2D. FIG. 2E shows another embodiment of attaching element 14 located in a section of primary shaft 4, as a clamp which accepts secondary cylinder 6.

Figure 2F:
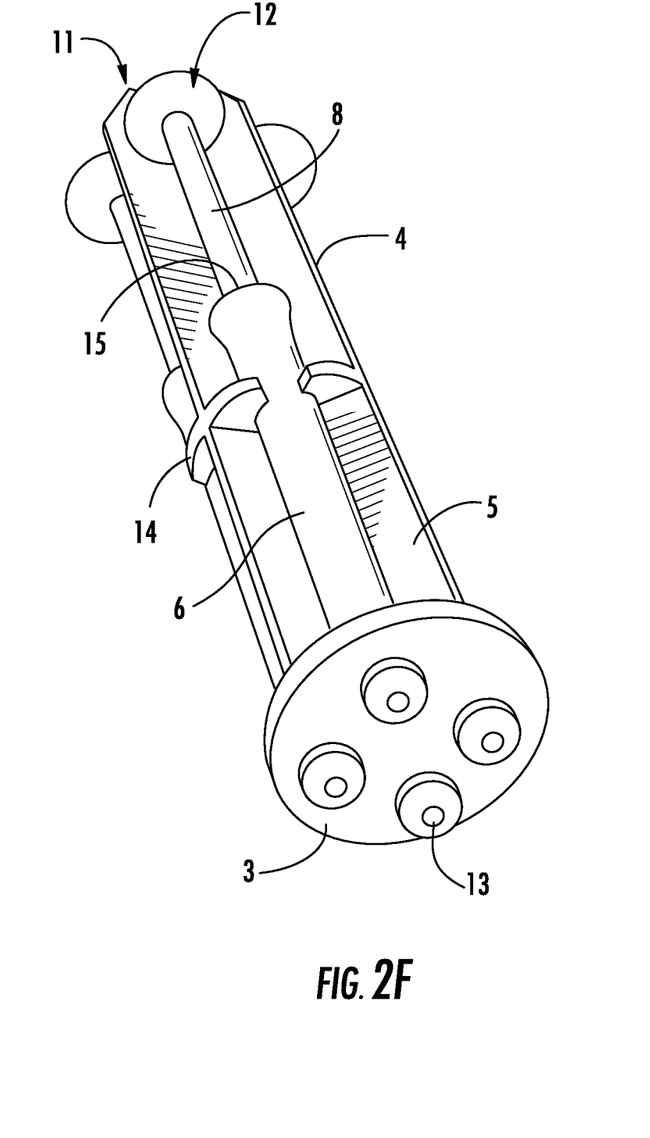
FIG. 2F is a front perspective view a sixth embodiment of the novel combining syringe.

Moreover, as best indicated in FIG. 2F, secondary cylinder 6 has a dispensing end 13 that is inserted through primary plunger 3. When an administrator applies a force to the secondary pressure applying end 13 of the secondary plunger shaft 8, fluid is dispensed through the primary plunger 3.

In all of these exemplary configurations, it should be understood that the specific syringes disclosed herein may take many form of many sizes that are well-known in the combining syringe art and all of such alternative forms are within the scope of this invention. For example, 20 ml., 30 ml., or 60 ml. size syringes may be used as the large syringe and a 0.5 ml. sized syringe may be used as the small syringe.

It will thus be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

Now that the invention has been described,

The invention claimed is:

1. A combining syringe comprising:
   a first cylinder having an attaching end opposite of a first plunger receiving end, comprising:
   a first plunger shaft having a longitudinal body whereby a first plunger attaching end is located opposite of a first pressure applying end;
   said first plunger shaft having an attaching element, whereby, said attaching element is configured to be retained within said first cylinder when said first plunger shaft is depressed into said first cylinder; and,
   a first plunger connected to said first plunger attaching end of said first plunger shaft;
   a second cylinder having a dispensing end located opposite of a second plunger receiving end, said second cylinder is configured to dispense a fluid through said first plunger when a portion of said second cylinder is inserted through said first plunger, whereby, said portion of said second cylinder protrudes an end of said first plunger;
   a second plunger shaft having a longitudinal body whereby a second plunger attaching end is located opposite of a second pressure applying end;
   said second plunger receiving end of said second cylinder and said second pressure applying end of said second plunger shaft configured to be located between said first pressure applying end of said first plunger shaft and said first plunger;
   a second plunger connected to said second plunger attaching end of said second plunger shaft;
   said second plunger conforming to an inner cylinder wall within said second plunger receiving end of said second cylinder, said second plunger positioned to create a pressure great enough to force a fluid through said first plunger when a force is applied to said second pressure applying end of said second plunger shaft, said second plunger shaft is configured to be depressed in a location between said first pressure applying end and said first plunger of said first plunger shaft, and;
   said first plunger conforming to said inner cylinder wall within said first plunger receiving end of said first cylinder, said first plunger positioned to create a pressure great enough to force a fluid out of said first cylinder when a force is applied to said first plunger shaft.

2. The combining syringe of claim 1, wherein said first cylinder has a leur-lock connection fitting located on said first cylinder attaching end.

3. The combining syringe of claim 2, wherein said first cylinder attaching end has a needle adapted to attach with said connection fitting.

4. The combining syringe of claim 2, wherein said first cylinder has tubing adapted to attach with said connection fitting.

5. The combining syringe of claim 1, wherein said first plunger shaft has at least one section to accommodate said second cylinder.

6. The combining syringe of claim 5, wherein said attaching element is a clamp to secure said second cylinder.

7. The combining syringe of claim 1, wherein said first plunger has at least one opening to receive dispensing end of said second cylinder.

8. The combining syringe of claim 7, wherein said opening has a plurality of reliefs radiating from its circumference.

9. The combining syringe of claim 1, wherein said first plunger is a pliable material with a range between 30 Shore A durometer and 60 Shore A durometer.

10. The combining syringe of claim 1, wherein a plurality of cylinders are configured to dispense fluid through said first plunger.

11. The combining syringe of claim 10, wherein said plurality of cylinders are of a variety of diameters.

12. The combining syringe of claim 1, wherein said second cylinder is connected to said first plunger shaft, whereby, said attaching element is located in a substantially central portion of said first plunger shaft.

13. A method of preparing a combining syringe, comprising the steps of:
   filling a first cylinder with a first fluid;
   configuring a first plunger shaft to accept a second cylinder of a second fluid;
   connecting attaching element of said first plunger shaft to said second cylinder, whereby, said attaching element is configured to be retained within said first cylinder when said first plunger shaft is depressed into said first cylinder;
   installing a dispensing end of said second cylinder containing said second fluid into an opening of a first plunger when a portion of said second cylinder is inserted through said first plunger, whereby, a portion of said second cylinder protrudes an end of said first plunger;
   inserting said first plunger into a first plunger receiving end of said first cylinder;
   applying a force to a second pressure applying end of a second plunger shaft to dispense said second fluid through said first plunger into said first cylinder, whereby, said second plunger shaft is configured to be depressed in a location between a first pressure applying end and said first plunger of said first plunger shaft; and, applying a force to said first pressure applying end of said first plunger shaft to dispense the combined solution through an attaching end of said first cylinder.

14. The method of preparing a combining syringe of claim 13, wherein an administrator inserts said second cylinder dispensing end into an end of said first cylinder.

15. The method of preparing a combining syringe of claim 13, wherein an administrator attaches at least one syringe into a clamp of said first plunger shaft.

16. The method of preparing a combining syringe of claim 13, wherein attaching
element is a clamp which secures said second cylinder to said first plunger shaft.

17. The method of preparing a combining syringe of claim 13, wherein an administrator selects a third cylinder based on a third plunger shaft having a different color than the said second plunger shaft.

18. The method of preparing a combining syringe of claim 13, wherein said opening has a plurality of reliefs radiating from its circumference.

19. The method of preparing a combining syringe of claim 13, wherein connecting said second cylinder to said first plunger shaft with said attaching element in a substantially central portion of said first shaft.

\* \* \* \* \*